United States Patent [19]
Davey et al.

[11] Patent Number: 5,847,239
[45] Date of Patent: Dec. 8, 1998

[54] TRANSESTERIFICATION PROCESS

[75] Inventors: Paul Nicolas Davey; Clive Derek Richardson; Christopher Paul Newman; Barrie R. Hart, all of Ashford, Great Britain

[73] Assignee: Quest International B.V., Naarden, Netherlands

[21] Appl. No.: 785,832

[22] Filed: Jan. 15, 1997

[30] Foreign Application Priority Data

Jan. 15, 1996 [GB] United Kingdom ................. 96300275

[51] Int. Cl.$^6$ ....................................... C07C 27/02
[52] U.S. Cl. ........................... 568/877; 568/876; 560/234
[58] Field of Search ...................... 568/876, 877

[56] References Cited

U.S. PATENT DOCUMENTS 2,840,599  6/1958  Somerville et al. .
2,902,510  9/1959  Webb .
4,927,954  5/1990  Knopf ..................................... 558/441

OTHER PUBLICATIONS

Chemical Abstracts, vol. 106, No. 3, abstract No. 18872c (Jan. 19, 1987).

CA 84: 165069.

*Primary Examiner*—Paul J. Killos
*Attorney, Agent, or Firm*—Pillsbury Madison & Sutro LLP

[57] ABSTRACT

Dihydromyrcene is reacted with a carboxylic acid, eg acetic acid, to produce an ester which is then reacted with an alcohol in a transesterification reaction to produce (dihydro) myrcenol and another ester. The preferred alcohol is 4-tertiarybutylcyclohexanol. Myrcenol can be produced in a similar way.

14 Claims, 2 Drawing Sheets

TRANSESTERIFICATION PROCESS

FIELD OF THE INVENTION

This invention concerns a transesterification process, particularly for making dihydromyrcenol (DHMOL) or myrcenol.

BACKGROUND TO THE INVENTION

Dihydromyrcenol is a well known fragrance material, which is used increasingly in the fragrance industry. Based on a turpentine feedstock, DHMOL can be made by the hydration of dihydromyrcene (citronellene), and this is currently done commercially using large quantities of strong aqueous sulphuric acid. This reaction converts the dihydromyrcene to DHMOL and also produces dilute sulphuric acid as a by product stream. Disposal of the waste dilute sulphuric acid in an economical and/or environmentally acceptable way can present difficulties.

A possible alternative approach to production of DHMOL is hydration of dihydromyrcene using alternative catalysts of acid clays, zeolites etc, and many attempts at such processes have been reported in the literature. The processes have, however, been found to be low yielding because of mixing/phase transfer/reactivity difficulties and are not cost effective.

The present invention provides an alternative approach to the production of dihydromyrcenol or the related material myrcenol. For brevity the term "(dihydro)myrcenol" will be used to refer to dihydromyrcenol or myrcenol. Similarly, the term "(dihydro)myrcene" will be used to refer to dihydromyrcene or myrcene.

SUMMARY OF THE INVENTION

According to one aspect of the present invention there is provided a process for preparing (dihydro)myrcenol from a (dihydro)myrcenyl ester by reacting this ester in a transesterification reaction with an alcohol to produce (dihydro)myrcenol. The (dihydro)myrcenyl ester may in turn be produced by reacting (dihydro)myrcene with a carboxylic acid.

The carboxylic acid used for producing the (dihydro)myrcenyl ester is not critical. Good results have been obtained using acetic acid, but other acids such as propionic acid, butyric acid, isobutyric acid etc. may alternatively be used.

The (dihydro)myrcenyl ester producing reaction can be effected in the presence of any suitable catalyst, but preferably a solid catalyst such as an ion-exchange material is used. Sulphonic acid cross linked polystyrene ion-exchange resins are well suited to this purpose. Good results have been obtained with the hydrogen ion-exchange resin Purolite CT 169 (Purolite is a Trade Mark).

The ester-producing reaction can be carried out at a range of temperatures, but preferably as low as possible while maintaining a liquid phase (eg 15°–20° C.), as this is found to give good selectivity of reaction. Conversion in the system is generally low and the materials are preferably passed through a fractionating column, with the ester product being collected as a non-volatile from the evaporator/re-boiler, and the remaining non-reacted materials being recycled to the catalyst in a continuous process.

In the transesterifiction reaction an alcohol and the (dihydro)myrcenyl ester react together in an equilibrium reaction, resulting in production of the desired (dihydro)myrcenol and the ester derived from the starting alcohol (product ester). The (dihydro)myrcenyl ester is preferably the acetate.

The transesterification reaction is preferably carried out in the presence of a suitable catalyst. Alkoxides, such as sodium methoxide, work well. Other possible catalysts include butyl titanates, isopropyl titanates and others known to those skilled in the art.

Either the (dihydro)myrcenol or the product ester preferably has the lowest boiling point of all materials taking part in the reaction in which case it can be readily collected by being distilled off. This has the beneficial effect of driving the equilibrium of the transesterification reaction in the desired direction. Also, the boiling points of the (dihydro) myrcenol and the product ester preferably are sufficiently apart from each other, and from those of the starting (dihydro)myrcenyl ester and the starting alcohol, to enable the reaction products to be separated from each other and from the starting materials by distillation. Thus, the differences in boiling point should be at least 2° C. at the distillation pressure used, preferably at least 5° C. Furthermore, the starting alcohol and the product ester should not decompose at the reaction temperature chosen. The temperature for the transesterification reaction is preferably chosen below 300° C., more preferably below 250° C., even more preferably below 180° C., most preferably at or below 150° C. The distillation of the reaction products is preferably, but not necessarily, carried out from the same vessel in which the transesterification reaction takes place. The distillation is preferably carried out under reduced pressure.

Very suitable alcohols for this purpose are tertiary-butylcyclohexanols, particularly 4-tertiary-butylcyclohexanol (PTBCH) and 2-tertiary-butylcyclohexanol.

In a preferred embodiment reaction of dihydromyrcenyl acetate (DHMAc) with PTBCH produces DHMOL and 4-tertiary-butylcyclohexyl acetate (PTBCHA).

PTBCHA is itself a useful material, that is usually prepared from the corresponding alcohol PTBCH by reaction with acetic acid, acid chloride or acetic acid anhydride in a process that also results in production of aqueous effluent (eg. acetic acid waste) that could present environmental and cost issues in disposal/recycle. In contrast, the present invention can produce two useful materials, eg. DHMOL and PTBCHA, in a way that does not also produce undesirable or difficult to dispose of waste products.

The present invention provides a much more efficient route for production of DHMOL and PTBCHA than the present processes for producing these materials. Comparing these routes by the "atom utilisation" approach of Sheldon (Roger A Sheldon, Industrial Environmental Chemistry, pp 99–119 Ed. D. T. Sawyer and A. E. Martell, and Roger A Sheldon, Chem & Ind 1992, pp 903–906), the process of the present invention has a theoretical atom utilisation approaching 100% while the current process for DHMOL production has a theoretical atom utilisation in the range 40 to 60% and the current process for PTBCHA production has a theoretical atom utilisation in the range 60 to 80%. The process of the invention is thus chemically efficient, and is also efficient in processing terms. For example, no costly wash stages are required.

The process of the invention also has the advantage that DHMOL can be produced without also producing waste dilute sulphuric acid, and PTBCHA can be produced without also producing aqueous effluent for disposal, in contrast to the typical procedures for producing these materials.

The present invention also includes within its scope (dihydro)myrcenol produced by the process of the invention, and PTBCHA produced in preferred embodiments of the invention.

Production of DHMOL and PTBCHA from dihydromyrcene (DHM) and PTBCH, will now be described by way of illustration in the following Example and by reference to the accompanying

EXAMPLE

1. The synthesis of dihydromyrcenyl acetate from dihydromyrcene and acetic acid.

Figure 3:
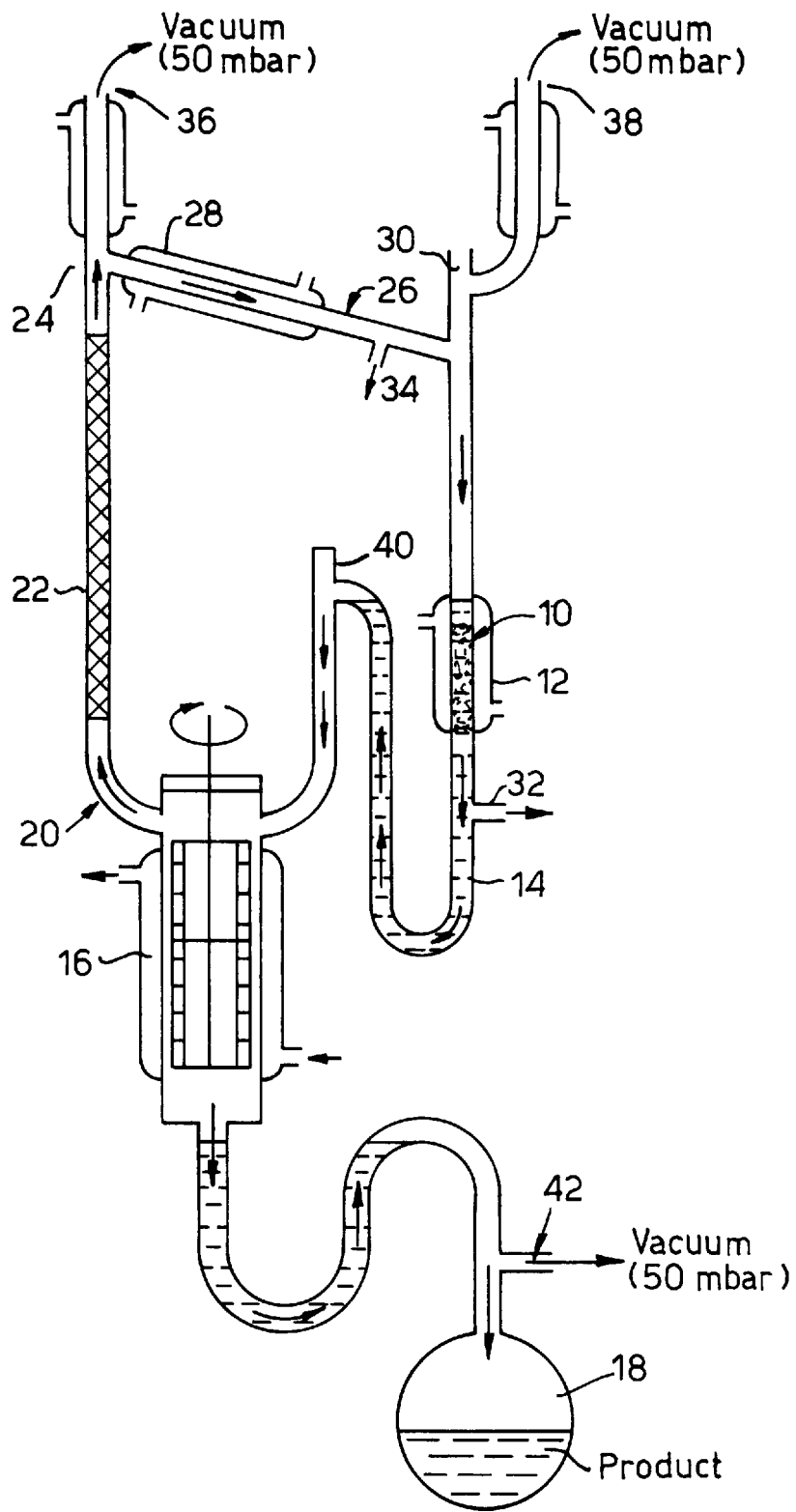
FIG. 3 shows laboratory scale equipment for reaction of DHM with acetic acid to produce DHMAc.

The reaction was carried out using the equipment shown in FIG. 3 which comprises a recirculating system for continuous processing. The equipment includes a catalyst bed 10 of 14 g of Purolite CT 169 (from Purolite) hydrogen ion-exchange resin packed in a jacketed column 12. Tubing 14 leads from the bottom of column 12 to a modified wiped film evaporator 16, including a collecting flask 18. Tubing 20 leads from evaporator 16 to a fractionating column 22, b ½ inch (13 mm) in diameter and 350 mm high, containing knitmesh packing (about 7 theoretical plates). A reflux ratio controller 24 is located at the top of column 22. Tubing 26 leads from reflux controller back to the catalyst bed, and includes a condenser cooling jacket 28. A sample inlet is provided at 30, with sample offtakes at 32 and 34. For practical convenience in the laboratory, the process is carried out at a vacuum of 50 mbar, and openings 36, 38 and 42 lead to vacuum pumps (not shown), with opening 40 leading to a vacuum gauge (not shown). Opening 42 is a liquid vapour lock.

The reaction is carried out as a continuous process (5–10% conversion) which feeds into wiped film evaporator 16. Product takeoff is mainly dihydromyrcenyl acetate at the bottom of the column, while a recycle stream from the top of the column mixes with the feed, and goes back into the catalyst bed reactor 10.

Considering matters in more detail, 1:1 (mol/mol) homogenous mixture of dihydromyrcene (with purity of about 89%) and glacial acetic acid (with purity of 99%+) was made up in a suitably sized container. This mixture was pumped into inlet 30 for passage at a rate of 0.4 ml/min through the catalyst bed 10 which had been previously packed into jacket column 12. The temperature in column 12 was held at 15°–20° C., by means of a ethylene glycol circulating bath.

The effluent that emerged from the bottom of the column was fed via tubing 14 into modified wiped film evaporator 16, which was held at a temperature of 150° C. The crude reaction mixture was separated up the fractionating column 22. The reflux ratio controller was used to achieve a reflux ratio of 1:1. The temperature in the condenser cooling circuit was held at 5° C. The starting materials (recycle stream) were fed back round to the top of the catalyst bed 10 and the product (DHMAc) was collected from the bottom of the evaporator in flask 18. The reaction gives a conversion of 5–10% per pass.

Typical composition of the product is:
92% Dihydromyrcenyl acetate,
2% Dihydromyrcenol,
3% Cyclademyl acetate,
3% Dihydromyrcene.

2. The transesterification of dihydromyrcenyl acetate with 4-tertiarybutylcyclohexanol.

Figure 1:
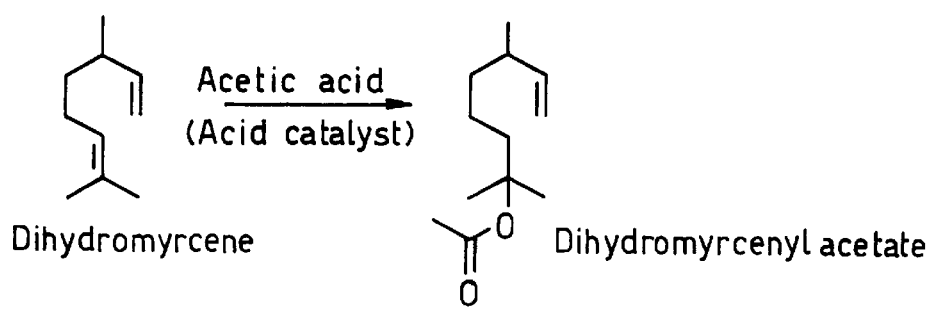
FIG. 1 shows the reaction of DHM with acetic acid to produce dihydromyrcenyl acetate (DHMAc)
Figure 2:
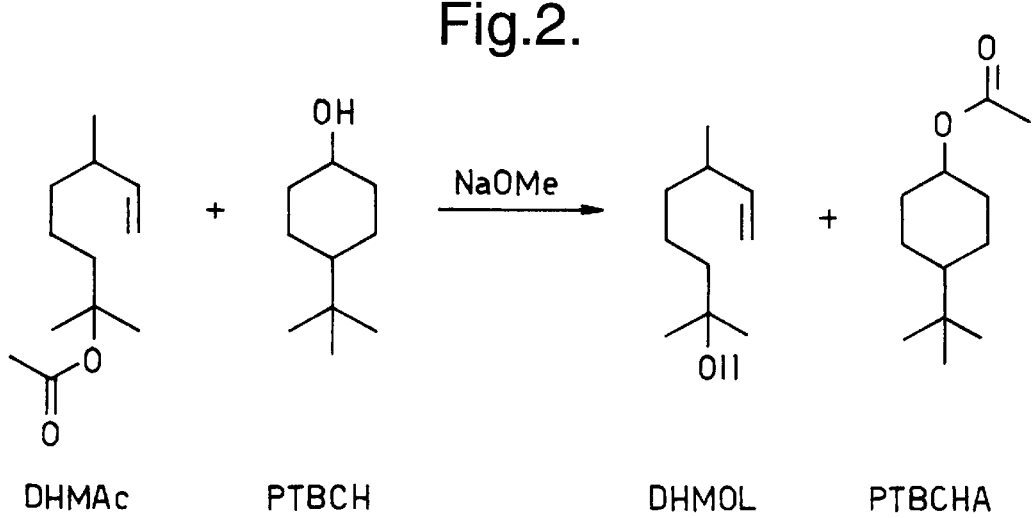
FIG. 2 shows the transesterification reaction of DHMAc with PTBCH in the presence of sodium methoxide catalyst to produce DHMOL and PTBCHA.

The reaction involved is shown in FIG. 2.

Laboratory Procedure 468 g (3.0 mol) PTCHB (26% cis, 65% trans) and 10.6 g (0.2 mol) solid sodium methoxide were charged to a 2 liter, 3-necked distillation flask fitted with a nitrogen bleed and thermometer. The flask was attached to a 1000 mm×50 mm fractioning column packed with stainless 'EX' Sulzer mesh packing and heated under vacuum (20 mb) for 0.5 hrs to a pot temperature of 112° C. in order to form the PTBCH alkoxide and remove the thus formed methanol. The still was then allowed to cool to 50° C., brought to atmospheric pressure and 594 g (3.0 mol) dihydromyrcenyl acetate (97% pure) added. Vacuum was then re-applied and the distillative transesterification completed. A summary of the distillation is given in Table 1.

The reaction has also been carried out in a pilot plant.

Pilot Plant

4-Tertiary-butylcyclohexanol, dihydromyrcenyl acetate and sodium methoxide were charged to a 100 liter scale distillation unit fitted with a fractionation column and heated to reflux. A small heads fraction for recycle (0.5% m/m of the charge) was removed at a reflux ratio of 5:1 (head pressure: 30 mbar, head temperature: 85° C.). A second fraction was removed at a reflux ratio of 5:1, head pressure of 20 mbar and head temperature of 98° C. as dihydromyrcenol product (34.5% m/m of the charge). At this point the head temperature started to rise and the reflux ratio was changed to 20:1 and a recycle fraction removed at a head temperature of 120° C. (19.0% m/m of the charge). A final fraction was then removed at total take-off at a head pressure of 10 mbar as 4-tertiarybutyl-cyclohexyl acetate product until the pot temperature rose to 150° C. (43.5% m/m of the charge).

TABLE 1

| Product | Pressure (m bar) | Head Temp (°C.) | Mass (g) | Purity % |
|---|---|---|---|---|
| Heads | 20 | <88 | 18.4 | — |
| DHMOL | 20 | 88–89 | 392.7 | 96.4 |
| Inters | 20 | 89–115 | 232.6 | 24.2 (DHMOL) |
|  |  |  |  | 46.7 (PTBCHA) |
| PTBCHA | 20 | 115–118 | 272.6 | 98.8 |
| Tails | 5 | 100 | 97.1 | 98.7 (PTBCHA) |
| Residue | — | — | 42.9 | — |

We claim:

1. A process for preparing (dihydro)myrcenol comprising reacting a (dihydro)myrcenol ester of acetic, propionic, butyric or isobutyric acid, with an alcohol in a transesterification reaction to produce (dihydro)myrcenol.

2. A process according up to claim 1, wherein the (dihydro)myrcenyl ester is the acetate.

3. A process according to claim 1, wherein the transesterification reaction is carried out in the presence of a catalyst, preferably an alkoxide catalyst.

4. A process according to claim 1 wherein (dihydro) myrcenol or the product ester are removed from the reaction mixture by distillation.

5. A process according to claim 1, wherein the alcohol is chosen such that the boiling points of the (dihydro)myrcenol and the ester produced in the transesterification reaction are at least 2° C. apart from each other, and from those of the starting (dihydro)myrcenyl ester and the starting alcohol at the distillation pressure.

6. A process according to claim 1 wherein the transesterification reaction is carried out below 300° C.

7. A process according to claim 1, wherein the alcohol is 4-tertiarybutylcyclohexanol or 2-tertiarybutylcyclohexanol.

8. A process according to claim 1 wherein the (dihydro)myrcenyl ester is produced by reacting (dihydro)myrcene with acetic acid.

9. A process according to claim 8, wherein the ester-producing reaction is effected in the presence of a solid catalyst.

10. A process according to claim 9, wherein the solid catalyst is an ion-exchange catalyst.

11. A process according to claim 8, wherein the ester-producing reaction is carried out as a continuous process at a temperature consistent with a liquid phase reaction.

12. A process according to claim 8, wherein dihydromyrcene is reacted with acetic acid to produce dihydromyrcenyl acetate, which is then reacted with 4-tertiarybutylcyclohexanol to produce dihydromyrcenol and 4-tertiarybutylcyclohexyl acetate.

13. A process according to claim 1 wherein the transesterification reaction is carried out at a temperature below 250° C.

14. A process according to claim 11 wherein the ester-producing reaction is carried out at a temperature in the range of 15°–20 ° C.

* * * * *